United States Patent [19]

Kochis

[11] Patent Number: 4,526,542

[45] Date of Patent: Jul. 2, 1985

[54] DENTAL BURR AND METHOD OF PREPARING A TOOTH

[76] Inventor: Robert Kochis, 39 Elaine St., Trumbull, Conn. 06611

[21] Appl. No.: 577,211

[22] Filed: Feb. 6, 1984

[51] Int. Cl.³ ............................................... A61C 3/02
[52] U.S. Cl. .................................... 433/165; 433/223; 408/202
[58] Field of Search ............... 433/165, 166, 223, 215; 408/202

[56] References Cited

U.S. PATENT DOCUMENTS

| | | | |
|---|---|---|---|
| 412,952 | 10/1889 | Elterich | 408/202 |
| 716,441 | 12/1902 | Latham | 408/202 |
| 2,280,927 | 4/1942 | Phillips | 433/165 |
| 2,855,673 | 10/1958 | Gruenwald | 433/166 |
| 3,073,031 | 1/1963 | Brenman et al. | 433/166 |
| 3,645,642 | 2/1972 | Koslow | 408/202 |

FOREIGN PATENT DOCUMENTS 302233 12/1954 Switzerland ..................... 408/202

Primary Examiner—John J. Wilson
Attorney, Agent, or Firm—Arthur T. Fattibene

[57] ABSTRACT

An improved dental burr and method of preparing a tooth for a porcelain to metal restoration. The method comprises the forming of a test trough of a precise depth in the tooth enamel across a tooth and removing the necessary enamel from the rest of the tooth to a corresponding depth so as to provide the space necessary to accommodate the required thickness of the porcelain restoration. To secure the desired optimum depth, a dental burr is provided with a stop flange to limit the depth of the cut or trough. In one embodiment the stop flange is rendered detachable connected to the burr so as to render the burr useful for other procedures.

1 Claim, 10 Drawing Figures

DENTAL BURR AND METHOD OF PREPARING A TOOTH

FIELD OF INVENTION

This invention relates to a dental burr and in a method of preparing a tooth in a procedure of a restoration made with procelain fused to metal.

PROBLEM & PRIOR ART

The preparation or reduction of a tooth to receive porcelain to metal restoration requires a precision greater than that generally required for conventional crown and bridgework procedures. This is because to obtain optimum structured and aesthetic results the metal and procelain are required to have certain minimal suggested thickness. Any excessive deviation for the minimal suggested thickness invariably will result in a restoration that will inevitably cause problems. Therefore, dentist heretofore encountered some difficulty in preparing a tooth within the suggested minimal thickness, since such distances were visually gauged.

While various boring tools constructing are known to limit the depth of a bore or drill hole as evidenced by U.S. Pat. Nos. 716,441; 2,317,615; 3,645,642; 3,762,052; 4,039,266 and 4,345,899, such tools had only industrial application in which the problems and considerations are radically distinct from those encountered in dentistry, and for these reasons are not suitable for performing a dental procedure.

OBJECTS

An object of this invention is to provide a dental burr having a burr head which is limited to the precise penetration of the tooth structure necessary to effect an optional procelain to metal restoration.

Another object is to provide a method of preparing a tooth for a porcelain to metal restoration whereby a test trough is made in the tooth enamel to the precise optimum depth, and whereby the test trough functions as a guide or gauge for the dentist in removing the remaining surface of the tooth necessary for a given restoration.

Another object is to provide a dental burr which has specific application for a procelain to a metal restoration as well as general application for other procedures.

BRIEF SUMMARY OF THE INVENTION

The foregoing objects and other features and advantages are attained by a dental burr having a stop flange located thereon at a predetermined position whereby the flange will function to limit the penetration of the burr head to a precise predetermined depth or penetration of a tooth structure. In operation the burr head is used to define a test trough to a predetermined depth in the tooth structure; and which depth is automatically determined by the flange. The remaining tooth structure necessary for a particular restoration is removed to the same depth as is determined by the test trough created by the burr head.

In one form of the invention the stop flange is detachably connected to the burr head whereby upon removal of the flange, the burr head may be used to perform other procedures.

FEATURES

A feature of this invention resides in the provision of a dental burr having a stop flange predeterminately position thereon.

Another feature resides in a dental burr having a removable stop flange.

Another feature resides in the method of effecting a tooth restoration wherein a precise test trough is first formed in the tooth structured and which trough is then used as a visual guide for the dentist for effecting the removal of the remaining tooth structure to a precise degree for effecting the optimal minimal thickness for a procelain to metal restoration.

Other features and advantages will become more readily apparant when considered in view of the drawings and specification in which.

DETAILED DESCRIPTION

Figure 3:
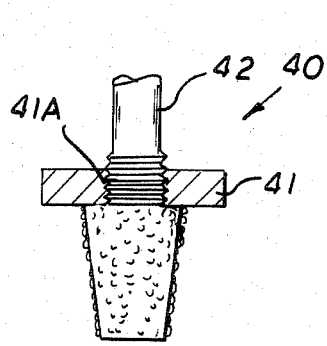
FIG. 3 is a side view of another modified embodiment.

Referring to the drawings there is illustrated therein several dental burrs embodying the present invention, and which burrs are particularly useful in precisely preparing a tooth for a procelain to metal restoration.

Figure 1:
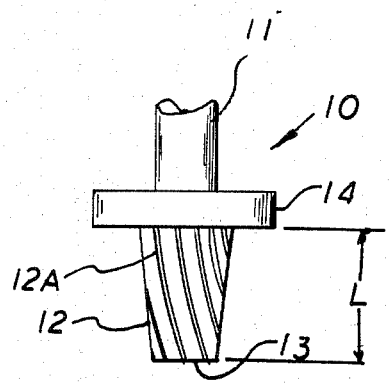
FIG. 1 is a side view of a dental burr embodying the invention.

In FIG. 1 there is disclosed a dental burr 10 which comprises a shank portion 11 which is readily adapted to be received in the of a dental drill. Connected to the end of the shank portion is a burr head 12 which as shown is provided with cutting edges 12A. In the illustrated enbodiment the free end of the burr head 12 is provided with a flat planar surface 13. Connected to the shank portion and immediately adjacent to the burr head is a stop flange 14 that extends radically thereof and which is disposed substantially in a plane parallel to the base or flat surface 13 of the burr head. The arrangement is such that the distance "L" between the stop flange and the base or flat surface 13 of the burr head 12 is equal to the depth of the test trough to be made in a tooth structure in the preparation thereof for a procelain to metal restoration. It will be understood that the distance "L" may vary between 0.25 mm. to 2 mm. For example, the burr head may be 0.25 mm, 0.5 mm, 1. mm., 1.5 mm or 2 mm., so as to provide a full range of sizes commonly encountered in practice. It will be understood that the dental burr 10 as herein described may be utilized in a set to cover the range of sizes from say 0.25 mm. to 2 mm. In such an event the respective burrs may be color coded so that each size can be readily accertained by the dentist.

To effect a tooth restoration a dentist utilizing a dental burr 10, as described will make a cut or test trough 20 across the tooth 19 preferably just above the crest of the gingival tissue to the prescribed depth "D" as determined by the distance "L" of the particular burr head 10 used. This may be done labially and lingually. Because of the flat bottom surface 13 and the depth determined by the stop flange 14, the dentist can quickly and automatically effect such test cut or trough 20 quickly and accurately to the desired depth; so as to provide for the optiomal porcelain veneering which should be of a thickness of 1 mm., axially and 1.5 mm. incusally and occlusally. A lesser thickness of procelain could create problems in obtaining a satisfactory color, and a greater thickness could result in a structural weakness within the porcelain that could result in cracking, either during the restoration or subsequent thereto. Therefore, it is essential that the depth of the test cut or trough be precise.

Once the precise depth of the test cut or trough 20 has been determined, the remainder enamel portion of the tooth 19 structure can be readily removed by the dentist to a precise degree by ready reference to the depth of the test cut or trough 20. Best seen in FIGS. 5 and 8, the precise amount of the tooth structure 19 has been reomved so as to allow for the optimal porcelain to metal thickness to be obtained.

Figure 9:
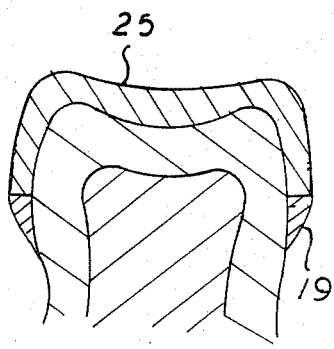
FIG. 9 is a section view on line 9—9 on FIG. 6.
Figure 8:
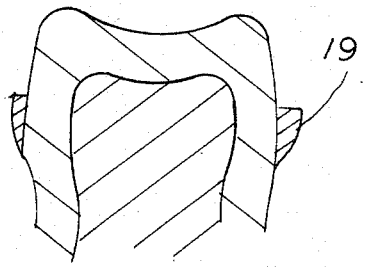
FIG. 8 is a section view taken on line 8—8 on FIG. 5.
Figure 7:
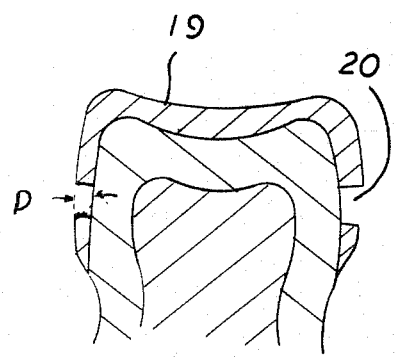
FIG. 7 is a section view taken in line 7—7 on FIG. 4.
Figure 6:
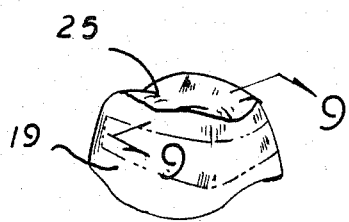
FIG. 6 is a perspective view of the restored tooth.
Figure 5:
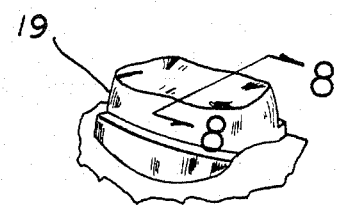
FIG. 5 is a perspective view of a tooth fully prepared for receiving a porcelain to metal restoration.
Figure 4:
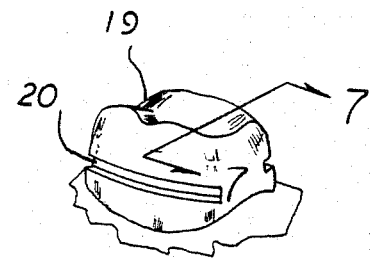
FIG. 4 is a perspective view of a tooth having a test trough formed therein in accordance with this invention.
Figure 10:
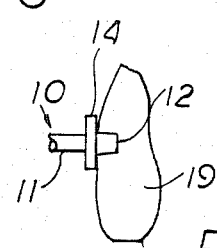
FIG. 10 is a schematic side view showing the dental burr as applied to an anterior tooth.

In FIGS. 5 and 8, the enamel of the tooth 19 has been removed to the depth of the cut or trough 20 which extends down to the dentin structure of the tooth. FIGS. 6 and 9 illustrate the porcelain to metal crown 25 properly positioned over the prepared tooth 19 as herein described.

Figure 2:
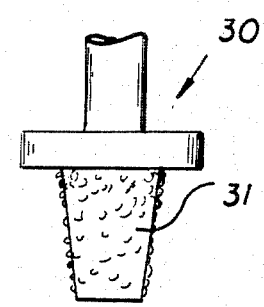
FIG. 2 is a side view of a modified embodiment.

FIG. 2 illustrates a modified burr construction. In this embodiment the construction of the burr 30 is identical to that described with respect to FIG. 1 except that the burr head 31 is coated with diamond chips to provide a diamond abrading surface. In all other respects the construction and operation of burr 30 is similar to that of FIG. 1.

FIG. 3 illustrates another embodiment of a dental burr 40. This embodiment is identical to that of FIG. 2 except that the flange 41 is detachably connected to the shank portion with a threaded portion 41A to which the flange 41 can be threaded and unthreaded relative thereto. It will be understood that the threaded portion 41A is spiraled in a direction opposite to that of the rotation of the burr 40. By effecting the removability of the stop flange 41, the burr 40 may be used as a conventional burr when the flange is removed, and with the flange 41 attached can be used to effect a porcelain to metal restoration as herein described.

It will be understood that the flange 14 of burr 10 may also be detachably connected as described with respect to FIG. 3.

While the invention has been described with respect to several particular embodiments thereof, it will be readily understood and appreciated that variations and modifications can be made without departing from the spirit or scope of the invention.

I claim:

1. A dental burr comprising a shank having a connected working burr head, said burr head having a predetermined length substantially equal to the depth of a test trough cut into a tooth, and a means to limit the penetration of said burr head during a tooth restoration procedure to the depth of the test trough, wherein said burr head is formed with a diamond abrading surface, said limit means including a laterally extending flange, and means for detachably connected said flange to the said shank of said burr, wherein said detachably connecting means includes complimentary threads formed on said flange and said shank whereby said flange is threaded to said shank, and said threads being threaded in a direction opposite to the rotation of said burr head.

* * * * *